United States Patent [19]

Albrecht et al.

[11] Patent Number: 4,594,096

[45] Date of Patent: Jun. 10, 1986

[54] PLANT PROTECTION AGENTS IN THE FORM OF MIXED DISPERSIONS

[75] Inventors: Konrad Albrecht, Kelkheim; Gerhard Frisch, Wehrheim, both of Fed. Rep. of Germany

[73] Assignee: Hoechst Aktiengesellschaft, Frankfurt am Main, Fed. Rep. of Germany

[21] Appl. No.: 573,402

[22] Filed: Jan. 24, 1984

[30] Foreign Application Priority Data

Jan. 27, 1983 [DE] Fed. Rep. of Germany ....... 3302648

[51] Int. Cl.$^4$ .............................................. A01N 25/02
[52] U.S. Cl. ................................... 71/93; 71/DIG. 1; 71/90; 71/94; 71/106; 71/108; 71/120; 71/121; 514/937; 514/183; 514/256; 514/398; 514/425; 514/493
[58] Field of Search ............... 71/DIG. 1, 93, 94, 106, 71/108, 120, 121; 424/251, 273, 274, 276, 288; 514/937

[56] References Cited

FOREIGN PATENT DOCUMENTS 17001 10/1980 European Pat. Off. .
33291 1/1981 European Pat. Off. .

*Primary Examiner*—Catherine L. Mills
*Attorney, Agent, or Firm*—Curtis, Morris & Safford

[57] ABSTRACT

The aqueous mixed dispersions, according to the invention, of pesticides, which contain an active compound concentrate, based on ($C_1$–$C_{12}$)-alkyl phthalates as the solvent, of one or more active compounds melting below 70° C., in combination with an aqueous suspension concentrate of one or more active compounds melting above 70° C., possess surprisingly high stability on storage.

5 Claims, No Drawings

PLANT PROTECTION AGENTS IN THE FORM OF MIXED DISPERSIONS

The present invention relates to liquid pesticidal preparations of mixtures of active compounds in the form of aqueous mixed dispersions containing active compounds melting below 70° C. in combination with active compounds melting above 70° C.

The following active compounds melting above 70° C. are particularly suitable:

herbicidal urea derivatives, such as Isoproturon[N,N-dimethyl-N'-(4-isoproylphenyl)-urea], linuron[N-(3,4-dichlorophenyl)-N'-methoxy-N'-methylurea], monolinuron[N-(4-chlorophenyl)-N'-methoxy-N'-methylurea] and diuron[N-(3,4-dichlorophenyl)-N',N'-dimethylurea];

herbicidal triazine derivatives, such as atrazine [2-chloro-4-ethylamino-6-isopropylamino-1,3,5-triazine], cyanazine[2-(4-chloro-6-ethylamino-1,3,5-triazin-2-yl-amino)-2-methylpropionitrile] and simazine[2-chloro-4,6-bis-ethylamino-1,3,5-triazine];

fungicidal active compounds, such as fentine hydroxide (triphenyltin hydroxide), Carbendazim (methylbenzimidazol-2-ylcarbamate) and captafol[3a,4,7,7a-tetrahydro-N-(1,1,2,2-tetrachloroethanethio)-phthalimide] and the insecticidal active compound endosulfane(6,7,8,9,10,10-hexachloro-1,5,5a,9a-tetrahydro-6,9-methano-2,4,3-benzodioxathiepine oxide).

The following are particularly suitable active compounds which melt below 70° C.:

herbicidal active compounds, such as trifluralin[2,6-dinitro-N,N-dipropyl-4-trifluoromethylaniline], Pendimethalin[N-(1-ethylpropyl)-2,6-dinitro-3,4-xylidine], dinoseb acetate(O-acetyl-2-sec-butyl-4,6-dinitrophenol) and Dowco 433 [isooctyl 4-amino-3,5-dichloro-6-fluoro-2-pyridineoxyacetate] and herbicidal phenoxypropionic acid esters, in particular Diclofop-methyl[methyl 2-(4-(2,4-dichlorophenoxy)-phenoxy)-propionate], ethyl 2-(4-(6-chloro-2-benzoxazolyloxy)-phenoxy)-propionate and ethyl 2-(4-(6-chloro-2-benzthiazolyloxy)-phenoxy)-propionate and the fungicidal active compound pyrazophos[2-(O,O-diethylthionophosphoryl)-5-methyl-6-carbethoxy-pyrazolo[1,5-a]pyrimidine].

The above-mentioned active compounds are all known. Where common names have been quoted, they are described in H. Martin, *The Pesticide Manual*, British Crop Protection Council, 6th edition 1979. The benzoxazolylphenoxypropionic acids and benzthiazolylphenoxypropionic acids are known from German Offenlegungsschrift No. 2,640,730. Isooctyl 4-amino-3,5-dichloro-6-fluoro-2-pyridineoxyacetate (Dowco 433) is described in European Patent Application No. 67,712.

The application of mixtures of active compounds in the form of so-called tank mixtures is known. A tank mixture is an aqueous dilution, brought to a specific concentration for application, of the two formulations of the individual active compounds, which can be in the form of an emulsion concentrate, a suspension concentrate or a wettable powder. In this case each of the formulations of the individual active compounds is accurately adjusted to suit its physical and chemical properties. This requires, relative to each particular active compound, a special selection of the solvents and of the system of auxiliaries, such as emulsifiers, dispersing agents or wetting agents. The incompatibility of the formulations to be employed frequently causes difficulties in such tank mixtures. Thus demixing, flocculation, the formation of agglomerates (resulting in the spray nozzles becoming blocked) or coagulation can occur, causing severe interruptions or completely preventing well-ordered application of the active compounds.

In order to eliminate this drawback, it is possible in principle to formulate the appropriate mixtures of active compounds together as finished formulations, in the form of an emulsion concentrate, a suspension concentrate or a wettable powder. However, the formulation of two or more active compounds by one mode of formulation is made difficult or completely impossible by differences in the physico-chemical properties of the active compound components, particularly in cases where there are considerable differences in the solubilities and melting points of the individual compounds. This applies very particularly to mixtures of solid and liquid active compounds.

It is known, in accordance with European Patent Application No. 17,001, that formulations of mixtures of active compounds can be prepared by mixing an aqueous suspension of active compound with a solid active compound. It is also known, in accordance with European Patent Application No. 33,291, to add a further active compound in a molten state to an aqueous suspension of active compound. These processes can, however, only be used for very particular systems of active compounds. Thus it is not possible by these processes to formulate the abovementioned active compounds melting below 70° C. with the abovementioned higher-melting active compounds. When the liquid, lower-melting active compound component is added to suspension concentrates of the higher-melting component, the solidifying particles of active compound coagulate together with the active compound particles present in the suspension concentrate. It has now been found, surprisingly, that aqueous suspension concentrates of active compounds melting above 70° C. form stable mixed dispersions with active compound concentrates of active compounds melting below 70° C. if the latter are formulated on the basis of ($C_1$–$C_{12}$)-alkyl phthalates as the solvent.

The present invention relates, therefore, to liquid pesticidal agents based on aqueous mixed dispersions, which contain an active compound concentrate, based on ($C_1$–$C_{12}$)-alkyl phthalates as the solvent, of one or more active compounds melting below 70° C., in combination with an aqueous suspension concentrate of one or more active compounds melting above 70° C.

The abovementioned pesticides are particularly suitable as active compounds. In this case the suspension concentrates are formulated with conventional formulation auxiliaries, particularly with those mentioned in German Offenlegungsschrift No. 2,924,403 and German Patent Application P No. 32 40 862.5.

The active compound concentrates are formulated with the aid of known emulsifiers, such as triethanolamine salts of a mixture of phosphoric acid monoesters and diesters of a tristyrylphenol polyglycol ether containing 18 units of EO*) (®Soprophor FL, Rhône Poulenc) or amine salts of ethoxylated polyacrylylphenols (preparation 10-D-12 ®, Rhône Poulenc) or polyglycol ethers of a phenolaldehyde or condensation products of alkylphenols with formaldehyde and polyamines (®Sandoperol A or ®Sandoperol SB, Sandoz) or a mixture of ionic and nonionic surfactants (®Atlox 4658, Atlas Chemie).

*)EO=ethylene oxide

A di-($C_4$ to $C_8$)-alkyl phthalate is preferably used as the ($C_1$-$C_{12}$)-alkyl phthalate. Aromatic solvents, such as, for example, ½-methylnaphthalene, ®Solvesso 100 (boiling point 162°–177° C.), ®Solvesso 150 (boiling point 187°–207° C.), ®Solvesso 200 (boiling point 219°–282° C.), can be added to the phthalic acid esters in an amount of up to 10% by weight, based on the phthalic acid ester employed.

In the case of suspension concentrates, the wetting agent employed is preferably an alkali metal salt of a phosphate partial ester of a ($C_6$-$C_{24}$)-alkyl polyglycol ether (containing 2–20 EO units). The dispersing agents employed are preferably alkali metal salts of sulfosuccinic acid half-esters, alkali metal ligninsulfonates or condensation products of formaldehyde and cresols. It is also possible to add to the suspension concentrate small quantities of an aluminum silicate having a lamellar structure of the bentonite type, such as, for example, ®Hectorite or montmorillonite, and also mixtures of equal parts of an alkali metal ligninsulfonate and a swellable alkaline earth metal silicate, as a thickener in accordance with German Patent Application P No. 32 40 862.5, and also small quantities of an antifoaming agent based on tributyl phosphate or on silicones, and small quantities of a polysaccharide, such as, for example, ®Rhodopel 23 (Rhône Poulenc). In addition an antifreeze agent, such as ethylene glycol, propylene glycol or glycerol, can be added.

The suspension concentrates comprise 5–55% by weight of active compounds, 2 to 30% by weight of dispersing agent, 0.1 to 5% by weight of thickener, 0.5 to 8% by weight of wetting agent and also 0.1 to 2% by weight of an aluminum silicate having a lamellar structure, 0.2 to 4% by weight of anti-foaming agent, 0 to 20% by weight of anti-freeze agent and 0.01 to 3% by weight of polysaccharide; the remainder up to 100% by weight is water. These aqueous suspensions are prepared in a conventional manner by wet grinding using frictional ball mills.

The active compound concentrates comprise 5 to 50% by weight of active compound, 10 to 80% by weight of phthalic acid ester and 2 to 20% by weight of emulsifiers.

The mixed dispersions according to the invention are prepared by adding the suspension and active compound concentrates described above to one another, with vigorous stirring, it being possible to select any desired mixing ratios.

It is preferable to select a ratio of suspension concentrate to active compound concentrate within the range from 0.1:5 to 5:0.1.

A few examples of possible combinations of active compounds for the mixed dispersions according to the invention are indicated below:

| Suspension concentrate | Active compound concentrate |
|---|---|
| diuron | Pendimethalin |
| diuron | trifluralin |
| diuron | Pendimethalin + trifluralin |
| atrazine + cyanazine | Pendimethalin |
| atrazine + cyanazine | trifluralin |
| atrazine + cyanazine | Pendimethalin + trifluralin |
| atrazine + simazine | Pendimethalin |
| atrazine + simazine | trifluralin |
| atrazine + simazine | Pendimethalin + trifluralin |
| simazine + cyanazine | Pendimethalin |
| simazine + cyanazine | trifluralin |
| simazine + cyanazine | Pendimethalin + trifluralin |
| diuron + Isoproturon | Pendimethalin |
| diuron + Isoproturon | trifluralin |
| diuron + Isoproturon | Pendimethalin + trifluralin |
| diuron + atrazine | Pendimethalin |
| diuron + atrazine | trifluralin |
| diuron + atrazine | Pendimethalin + trifluralin |
| Isoproturon | trifluralin |
| Isoproturon | Pendimethalin |
| Isoproturon | isooctyl (4-amino-3,5-dichloro-6-fluoro-2-pyridine)-oxyacetate |
| Isoproturon | trifluralin + Pendimethalin |
| Isoproturon | Diclofop-methyl |
| linuron | Diclofop-methyl |
| linuron | trifluralin |
| linuron | Pendimethalin |
| linuron | trifluralin + Pendimethalin |
| linuron | dinoseb acetate |
| captafol | pyrazophos |
| Carbendazim | pyrazophos |
| Carbendazim | Diclofop-methyl |
| fentine hydroxide | pyrazophos |
| fentine hydroxide | Diclofop-methyl |
| endosulfane | Diclofop-methyl |
| endosulfane | pyrazophos |
| atrazine | Pendimethalin |
| cyanazine | Pendimethalin |
| cyanazine | trifluralin |
| cyanazine | Pendimethalin + trifluralin |
| simazine | Pendimethalin |
| simazine | trifluralin |
| simazine | Pendimethalin + trifluralin |

Amongst these active compound combinations, the following should be mentioned preferentially: Isoproturon/trifluralin, Isoproturon/Pendimethalin, Isoproturon/Diclofop-methyl and captafol/pyrazophos; the combinations Isoproturon/trifluralin and Isoproturon Pendimethalin are particularly preferred.

The formulations according to the invention are surprisingly stable to heat and frost within the range of temperatures between −15° C. and +50° C. The formulations according to the invention exhibit no changes at all, such as precipitation, flocculation etc., even after one and a half to two years.

The formulation examples, 1 to 42, listed in the following table demonstrate the broad applicability of the invention.

TABLE

| COMPOSITION | 1 | 2 | 3 | 4 | 5 | 6 | 7 | 8 | 9 | 10 | 11 | 12 | 13 |
|---|---|---|---|---|---|---|---|---|---|---|---|---|---|
| Isoproturon suspension[1] | 34.5 | 40 | 79.2 | 34.5 | 59 | | | | | | | | |
| Linuron suspension[2] | | | | | | 40 | 40 | 55 | 40 | 40 | | | |
| Captafol suspension[3] | | | | | | | | | | | 58 | | |
| Carbendazim suspension[4] | | | | | | | | | | | | 8 | 56 |
| Trifluralin | 17.0 | | | 12 | | | 20 | | 15 | | | | |
| Pendimethalin | | 20 | | 10 | | | | 18 | 7 | | | | |
| Dowco 433 | | | 5.6 | | | | | | | | | | |
| Diclofop-methyl | | | | | 15.2 | 13 | | | | | | 20 | |
| Dinoseb acetate | | | | | | | | | | 20 | | | |
| Pyrazophos | | | | | | | | | | | | 15 | 16 |
| Endosulfane | | | | | | | | | | | | | |

TABLE-continued

| Examples; ingredients quoted in % by weight | | | | | | | | | | | | |
|---|---|---|---|---|---|---|---|---|---|---|---|---|
| Water | 20.1 | | 6.8 | 15.4 | 3.0 | 16.5 | 10 | 2 | 4 | 8 | 5 | 35 | 4 |
| RSoprophor FL | 9.1 | | 2.8 | 9.1 | 7.6 | 9.5 | 5 | 7 | 9 | 4.5 | 6 | 7 | 6 |
| Dioctyl phthalate | 19.3 | 20 | 5.6 | 19 | 15.2 | 21 | 25 | 18 | 25 | | 12 | 30 | 18 |
| ½ Methylnaphthalene | | | | | | | | | | | 4 | | |
| Dibutyl phthalate | | | | | | | | | | 27.5 | | | |
| RSandoperol A | | 20 | | | | | | | | | | | |

| COMPOSITION | 14 | 15 | — | 16 | 17 | 18 | 19 | 20 | 21 | 22 | 23 | 24 | 25 | 26 | 27 |
|---|---|---|---|---|---|---|---|---|---|---|---|---|---|---|---|
| Fentine hydroxide suspension[5] | 50 | 5 | | | | | | | | | | | | | |
| Endosulfane suspension[6] | | | | 8 | 60 | | | | | | | | | | |
| Atrazine suspension[7] | | | | | | 40 | | | | | | | | | |
| Cyanazine suspension[8] | | | | | | | 40 | 30 | 30 | | | | | | |
| Simazine suspension[9] | | | | | | | | | | 40 | 30 | 30 | | | |
| Diuron suspension[10] | | | | | | | | | | | | | 60 | 60 | 60 |
| Trifluralin | | | | | | | 18 | 12 | | 18 | 12 | | 5 | | 5 |
| Pendimethalin | | | | | 15 | 20 | | 18 | 20 | | 18 | 6 | | | 3 |
| Diclofop-methyl | | 20 | | | | | | | | | | | | | |
| Dinoseb acetate | | | | 30 | | | | | | | | | | | |
| Pyrazophos | 6 | | | | 15 | | | | | | | | | | |
| Endosulfane | | | | | | | | | | | | | | | |
| Water | 5 | 10 | | 18 | | 7 | 5 | 15 | | 5 | 15 | | 10 | 10 | 9 |
| RSoprophor FL | 7 | 15 | | 9 | 5 | 8 | 5 | 15 | 8 | 5 | 15 | 8 | 9 | 9 | 8 |
| Dioctyl phthalate | 22 | 50 | | 35 | 20 | 30 | 30 | | 32 | 30 | | 32 | 15 | 16 | 15 |
| ½ Methylnaphthalene | | | | | | | | | | | | | | | |
| Dibutyl phthalate | | | | | | | | | | | 22 | | | | |

| COMPOSITION | 28 | 29 | 30 | 31 | 32 | 33 | 34 | 35 | 36 | 37 | 38 | 39 | 40 | 41 | 42 |
|---|---|---|---|---|---|---|---|---|---|---|---|---|---|---|---|
| Isoproturon suspension[1] | | | | | | | | | | | | | | | 30 |
| Atrazine suspension[7] | 30 | 30 | 30 | 30 | 30 | 30 | | | | | | | | | |
| Cyanazine suspension[8] | 20 | 20 | 20 | | | | 30 | 30 | 25 | | | | 15 | 15 | |
| Simazine suspension[9] | | | | 20 | 20 | 20 | 30 | 30 | 25 | | | | | | |
| Diuron suspension[10] | | | | | | | | | | 30 | 30 | 30 | 40 | 40 | |
| Trifluralin | | 8 | 6 | | 8 | 8 | | 5 | 11 | | 10 | 10 | | | 12 |
| Pendimethalin | 10 | | 8 | 10 | 11 | 6 | 4 | 8 | 7 | 8 | | 8 | 8 | 10 | |
| Water | 13 | 20 | 7 | 9 | 11 | 8 | | 10 | | | | | | | |
| RSoprophor FL | | | 9 | 13 | 15 | 8 | | 17 | 3 | 22 | 21 | 6 | 10 | 10 | 20 |
| Dioctyl phthalate | 15 | 10 | 16 | 14 | | 20 | 14 | | 10 | 11 | 10 | 9 | 11 | 10 | |
| Xylene | | | 4 | | | | | | 19 | 14 | 14 | 22 | 16 | 15 | 25 |
| ½ Methylnaphthalene | | 2 | | | | | | | | | | | | | |
| RSandoperol A | | 10 | | | | | | | | | | | | | |
| RSandoperol 5 B | 12 | | | | | | | | | | | | | | |
| RSolvesso 150 | | | | 4 | | | 4 | | | | | | | | |
| RSolvesso 200 | | | | | 5 | | 14 | | | | | | | | 13 |
| RAtlox 4856 | | | | | | | | | | | | | | | |
| Preparation 10-D-12 | | | | | | | | | | | | | | | |

Suspensions 1–10 in the above table have the following composition:

(1)
- 46% by weight of active compound
- 7% by weight of a condensation product of formaldehyde and cresols
- 3% by weight of the sodium salt of a monoester/diester of a ($C_{12}$–$C_{18}$)-alkyl polyglycol ether-phosphate (®Forlanit P, Henkel KGaA)
- 2% by weight of anti-foaming agent
- 0.2% by weight of aluminum silicate powder (montmorillonite)
- 1% by weight of ®Darvan No. 3, Vanderbilt Corp., USA
- 5% by weight of ethylene glycol (2)
- 38% by weight of active compound
- 6% by weight of the Na salt of sulfosuccinic acid half-ester
- 1% by weight of bentonite
- 2% by weight of ®Forlanit P
- 1% by weight of anti-foaming agent
- 1% by weight of ®Darvan No. 3
- 2% by weight of glycerol (3)
- 44% by weight of active compound
- 10% by weight of the Na salt of sulfosuccinic acid half-ester
- 4% by weight of sodium ligninsulfonate
- 2% by weight of ®Hectorite
- 2% by weight of anti-foaming agent
- 1.3% by weight of ®Darvan No. 3

(4)
- 40% by weight of active compound
- 12% by weight of the Na salt of sulfosuccinic acid half-ester
- 2% by weight of Na ligninsulfonate
- 0.5% by weight of ®Darvan No. 3
- 2% by weight of anti-foaming agent
- 4% by weight of alkyl polyglycol ether
- 5% by weight of ethylene glycol (5)
- 41% by weight of active compound
- 11% by weight of the Na salt of sulfosuccinic acid half-ester
- 5% by weight of sodium ligninsulfonate
- 2% by weight of ®Darvan No. 3
- 2% by weight of ®Forlanit P
- 0.5% by weight of bentonite
- 6% by weight of ethylene glycol (6)
- 40% by weight of active compound 8% by weight of a formaldehyde/cresol condensation product
4% by weight of sodium ligninsulfonate
3% by weight of ®Forlanit P
1% by weight of ®Darvan No. 3
2% by weight of anti-foaming agent
0.1% by weight of polysaccharide (7)
45% by weight of active compound
11% by weight of the Na salt of sulfosuccinic acid half-ester
4% by weight of ®Forlanit P
2% by weight of anti-foaming agent
0.5% by weight of aluminosilicate powder (montmorillonite)
5% by weight of alkyl polyglycol ether (8)
45% by weight of active compound
11% by weight of a formaldehyde/cresol condensation product
5% by weight of Na ligninsulfonate
1% by weight of anti-foaming agent
0.05% by weight of polysaccharide
3% by weight of alkyl polyglycol ether (9)
45% by weight of active compound
13% by weight of the Na salt or sulfosuccinic acid half-ester
2% by weight of anti-foaming agent
1.5% by weight of ®Darvan No. 3
5% by weight of Na ligninsulfonate
3% by weight of polyglycol ether
0.2% by weight of polysaccharide
6% by weight of ethylene glycol

(10)
45% by weight of active compound
15% by weight of the Na salt of sulfosuccinic acid half-ester
1% by weight of anti-foaming agent
1% by weight of Forlanit P
0.2% by weight of polysaccharide
8% by weight of ethylene glycol
2% by weight of a formaldehyde/cresol condensation product
0.5% by weight of ®Hectorite The anti-foaming agent employed for the suspension was the silicone anti-foaming agent SE-2 made by Wacker-Chemie.

®Darvan No. 3 = a mixture of an Na salt of a ligninsulfonic acid with montmorillonite in equal parts.

The remainder up to 100% in the suspensions listed above is composed of water.

All the above-mentioned formulation compositions are outstandingly stable; they are fully effective biologically and exhibit no phytotoxicity.

COMPARISON EXAMPLES (a) For comparison, the following formulation was prepared in accordance with European Patent Application No. 33,291:
34.5% of an Isoproturon suspension[1] (see above), 20.1% by weight of water, 9.1% by weight of ®Soprophor FL and 19.3% by weight of dioctyl phthalate were initially taken. Molten trifluralin was added to this mixture, with stirring. A stable formulation was not obtained.

(b) 34,5% by weight of an Isoproturon suspension[1] (see above), 20.1% by weight of water, 9.1% by weight of ®Soprophor FL and 19.3% by weight of dicotyl phthalate were initially taken. Solid trifluralin was then stirred in, in accordance with European Patent Application No. 17,001. A stable formulation could not be obtained in this case either, since the active compound dissolved only partially.

(c) The same negative results were obtained if the abovementioned Isoproturon suspension was initially taken without ®Soprophor FL and dioctyl phthalate being present and if trifluralin in a solid or molten state was added, with stirring, in accordance with the two patent applications quoted above.

We claim:
1. A liquid stabilized pesticidal agent, which comprises a mixture of
   an active compound concentrate containing as the active ingredient one or more pesticidal compounds melting at a temperature below 70° C., said active compound concentrate containing 5 to 50% by weight of active ingredient, and as a solvent one or more dialkyl phthalates, each said alkyl being of from 4 to 8 carbon atoms, and
   an aqueous suspension concentrate containing as the active ingredient one or more pesticidal compounds melting above 70° C., said suspension concentrate containing 5 to 55% by weight of active ingredient, 2–30% by weight of a dispersing agent, an alkali metal salt of a sulfosuccinic acid half-ester, an alkali metal ligninsulfonate or a condensation product of formaldehyde and a cresol, 0.5 to 8% by weight of a wetting agent, an alkali metal salt of a phosphate partial ester of an alkyl polyglycol ester, which contains of from 2 to 20 ethylene oxide units and the alkyl of which is of from 6 to 24 carbon atoms, and 0.1 to 5% by weight of a thickener, a mixture of equal parts of an alkali metal ligninsulfonate and a swellable alkaline earth metal silicate, 10 to 80% by weight of phthalic acid ester, and 2 to 20% by weight of an emulsifying agent,
   the ratio of the amount of the active compound concentrate to the amount of the aqueous suspension concentrate being of from 0.1:5 to 5:0.1.

2. A liquid pesticidal agent as claimed in claim 1, wherein the active compound concentrate contains, as an emulsifying agent, triethanolamine salts of a mixture of phosphoric acid monoesters and diesters of a tristyrylphenol polyglycol ether containing 18 EO units, amine salts of ethoxylated polyacrylylphenols, polyglycol ethers of a phenolaldehyde, condensation products of alkylphenols with formaldehyde and polyamines or a mixture of ionic and non-ionic surfactants.

3. A liquid pesticidal agent as claimed in claim 1, wherein the suspension concentrates contain alkali metal salts of sulfosuccinic acid half-esters, alkali metal ligninsulfonates or condensation products of formaldehyde and cresols as the dispersing agent, alkali metal salts of phosphate partial esters of ($C_6$–$C_{24}$)-alkyl polyglycol ethers (containing 2–20 EO) as the wetting agent and mixtures of equal parts of an alkali metal ligninsulfonate and a swellable alkaline earth metal silicate as the thickener.

4. A liquid pesticidal agent as claimed in claim 1, which contains the active ingredient combination Isoproturon/trifluralin, Isoproturon/Pendimethalin, Isoproturon/Diclofop-methyl or captafol/pyrazophos.

5. A liquid pesticidal agent as claimed in claim 1, wherein the active ingredient in the active compound concentrate is trifluralin, Pendimethalin, dinoseb acetate, Diclofop-methyl, pyrazophos, isooctyl(4-amino-3,5-dichloro-6-fluoro-2-pyridine)-oxyacetate or endosulfane, and the active ingredient in the suspension concentrate is diuron, atrazine, cyanazine, simazine, Isoproturon, linuron, captafol, Carbendazim or fentine hydroxide.

* * * * *